United States Patent [19]

Mutter

[11] Patent Number: 5,139,344
[45] Date of Patent: Aug. 18, 1992

[54] METHOD AND APPARATUS FOR DEW POINT DETERMINATION

[76] Inventor: Arthur Mutter, Seminarstrasse 55, CH-5430 Wettingen, Switzerland

[21] Appl. No.: 745,273

[22] Filed: Aug. 12, 1991

Related U.S. Application Data

[63] Continuation-in-part of Ser. No. 358,541, May 30, 1989, abandoned.

[51] Int. Cl.[5] ............................................. G01N 25/66
[52] U.S. Cl. ............................................. 374/28; 73/73
[58] Field of Search ................... 374/18, 19, 20, 17, 374/27, 28; 73/335

[56] References Cited

U.S. PATENT DOCUMENTS

| | | | |
|---|---|---|---|
| 1,789,268 | 1/1931 | Anderson | 374/19 X |
| 2,376,209 | 5/1945 | Turin | 374/19 |
| 3,926,052 | 12/1975 | Bachtel | 374/20 X |
| 4,018,061 | 4/1977 | Williamitis | 73/335 X |
| 4,554,793 | 11/1985 | Harding, Jr. | 374/20 X |
| 4,589,274 | 5/1986 | Boyle | 374/28 |
| 4,799,235 | 1/1989 | Bannell et al. | 374/27 X |
| 4,877,329 | 10/1989 | Sauerbaum | 374/20 |
| 4,898,476 | 2/1990 | Herrmann et al. | 374/28 |

FOREIGN PATENT DOCUMENTS

| | | | |
|---|---|---|---|
| 0819648 | 4/1981 | U.S.S.R. | 374/20 |
| 0317306 | 8/1929 | United Kingdom | 374/20 |
| 2036339 | 6/1980 | United Kingdom | 374/19 |

*Primary Examiner*—Daniel M. Yasich
*Attorney, Agent, or Firm*—Schweitzer, Cornman & Gross

[57] ABSTRACT

A new method for determination of the dew-point of a humid gas by means of a light beam reflected by a dew-point mirror. During measurements of dew-points, particularly in the range between −50° C. to −95° C., excess moisture is added to the humid gas under measurement in the manifold. Thus the dew-point mirror is for a short period of time, impacted with a humid gas of higher water content. This results in a fast build-up of a layer of dew on the mirror. In the subsequent process of dew-point determination, this reduces the time of measurement significantly. For carrying out the method, a dew-point measuring device is described, which comprises a manifold with a by-pass circuit having a gas valve, an injector unit and a humidification unit. Particularly useful in the device is a humidification unit made of hygroscopic polyamide tube which ensures maintenance-free humidification of the gas by the water molecules diffusing into this tube from the ambient atmosphere.

13 Claims, 4 Drawing Sheets

METHOD AND APPARATUS FOR DEW POINT DETERMINATION

The present application is a Continuation-In-Part of application Ser. No. 358,541, filed May 30, 1989, now abandoned.

BACKGROUND OF THE INVENTION

The present invention relates to a method for determination of the dew-point of a humid gas by means of a light beam reflected by a mirror. It also relates to a device for carrying out the method.

A dew-point measuring instrument of the known type is described, e.g., in the Directions for Use K-1806 (December 1986 Edition) of MBW ELEKTRONIK AG, CH-5430 Wettingen.

Dew-point measurement is typically carried out by use of a cooled mirror, which is cooled by means of a Peltier element until a dew or hoar precipitate forms on the mirror. The cooling is controlled via photo-optical means until that temperature is reached at which a steady dew or hoar layer is achieved.

The problem of time consuming dew-point determinations arises with gases of low water content. Up to ten hours or more are required for the condensed water vapor on the mirror to become detectable.

Although this unsatisfactory situation has long been known, no practical solutions are known so far for accelerating the condensation of water vapor to dew and thus shortening the measurement time connected with dew-point determinations of gases of low water content.

It is, therefore, an object of the invention to improve the known method and the associated device for dew-point determination in such a way that a substantial acceleration would result in dew-point measurement of humid gases of low water content. Another object of the invention is to ensure the fault- and interference-free operation of dew-point measurement instruments in process engineering.

According to the method of the present invention, this improvement is achieved in that, during measurement of low temperature dew-points, preferably in the range between −50° C. to −95° C., moisture is added for short periods of time to the gas whose dew-point is to be determined (hereinafter the "humid gas sample") streaming in the manifold. The dew point mirror is thus in contact for short periods of time with a gas containing added moisture, so that an initial dew layer is rapidly produced on the dew-point mirror.

The associated device in a dew-point measuring instrument with a cooled dew-point mirror according to the invention comprises a gas valve which is arranged in the manifold supply line for the humid gas sample, upstream of which valve there are arranged an injector pump and a humidification unit, whereby added moisture may be added to a portion of the humid gas sample.

With the method according to the invention, extra moisture is inserted during the measurement process into the stream of the humid gas sample whose dew-point is to be determined. This is done automatically and only for a very short period of time, at a preselected mirror temperature. This temperature is selected to be in the vicinity of the expected temperature of the dew-point which is to be determined accurately. When this preselected temperature is below the temperature of the dew-point to be determined, a particularly fast measurement of dew-point is assured.

The humid gas sample, whose dew-point is to be determined, as such or with added excess moisture according to the method of the present invention, (with and without the addition of excess humidity) is advantageously led to and removed from the dew-point mirror via pressure lines.

The device according to the invention for carrying out the method is designed in such a way that the humidification unit, which temporarily adds excess moisture to the humid gas sample, is directly connected to and is driven by the gas removal line via a pressure line. This has the advantage of adding the excess humidity to the streaming humid gas sample without causing an interruption in, or interference to the gas flow.

The injector pump is preferably a positive-displacement pump, particularly a piston pump arranged in a pressure-proof housing. This arrangement has the advantage that it can be used at atmospheric as well as at higher pressures. An arrangement comprising a needle valve in conjunction with a non-return valve has proved satisfactory.

A particularly simple embodiment of a humidification unit consists of a hygroscopic tube, preferably a plastic tube. Water molecules from the atmosphere diffuse into the interior of the tube where they admix with the gas streaming through. Practical experience has indicated the usefulness, for this purpose, of a commercially available plastic tube which is absolutely maintenance-free.

Other advantages and features of the present invention will become more apparent hereinafter.

BRIEF DESCRIPTION OF THE DRAWINGS

There is shown in the appended drawings a presently preferred embodiment of the present invention wherein like numerals refer to like elements in the various view and wherein.

DETAILED DESCRIPTION OF THE INVENTION

Figure 1:
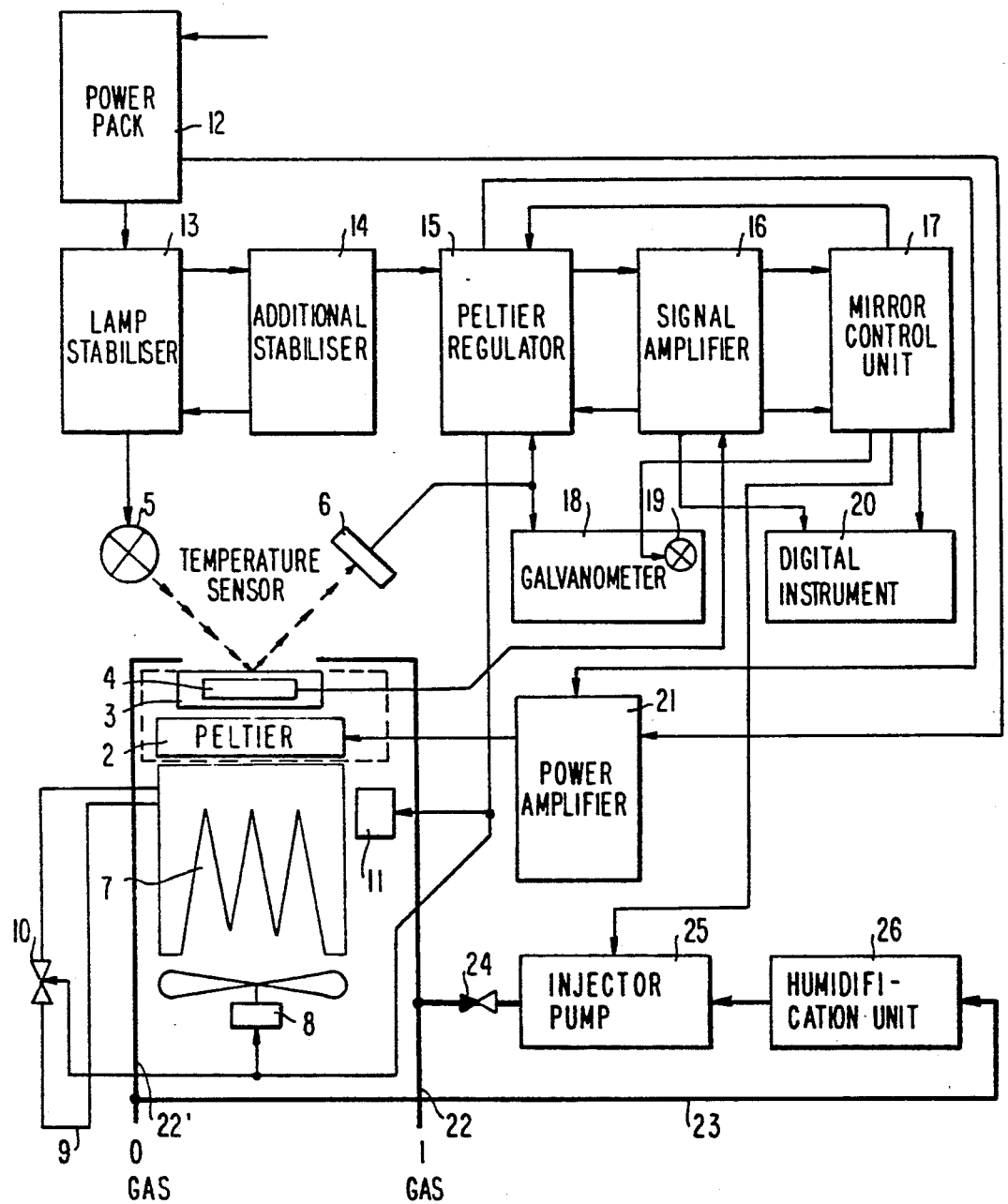
FIG. 1 shows the block diagram of a dew-point measuring device.

The dew-point measuring device schematically represented in FIG. 1 has a measuring head 1, essentially comprising a Peltier element 2 on the cold side which is of a dew-point mirror 3 with a built-in temperature sensor 4. The dew-point mirror 3 is illuminated by a measuring-head lamp 5, the reflected light being measured by a photoresistor 6. The waste heat produced by the Peltier element 2 is carried off by a water cooler 7 assisted by a fan 8. Both the water cooler 7 and the fan 8 are connected to a cooling-water loop 9 Cooling water supply is controlled by means of a water valve 10. Freon cooling may replace the water cooler 7 and the fan 8. Such cooling has an effective range of between +80° C. to −95° C. and possesses the additional advantage of being independent of cooling water.

The dew-point mirror 3 is associated with a heating arrangement 11, in order to facilitate measurement of dew points that are higher than ambient temperature. A power pack 12 comprises a transformer and a heavy-duty rectifier, and supplies the required current for the Peltier element 2 and the voltage for the measuring-head lamp 5 and the other electronic components. A lamp stabilizer 13 is directly connected with the power pack 12 and stabilizes the supply voltage for the lamp 5 to a high degree of precision, so that the measurement results will not be affected by variations in the brightness of the lamp 5. An additional stabilizer 14, connected to the lamp stabilizer 13, supplies the required auxiliary voltages of 4–15 Volt d.c. for the Peltier regulator 15, a temperature-sensor signal amplifier 16 and an automatic mirror control unit 17.

A galvanometer 18, e.g. a moving-coil instrument with a built-in signal lamp 19, indicates the light intensity reflected by the dew-point mirror 3. With heating, automatically triggered by the mirror control unit 17, the signal lamp lights up. Heating is effected by the Peltier element 2 operated in reverse. This causes the dew-point mirror 3 to be regularly relieved of the dew- or hoar layer, as extraneous distillates in the sample gas may produce undesirable condensates on the dew-point mirror 3, which falsify measurement results. This periodic operation is pre-programmed in a per se known manner and does not affect measurement as such.

A digital instrument 20 indicates the temperature determined by the temperature-sensor signal amplifier 16 and is at the same time connected with the automatic mirror control unit 17, with the aid of which the result of a dew-point measurement is retained when the dew-point mirror 3 is heated.

A power amplifier stage 21 is directly connected to the power pack 12 and supplies the necessary current for the Peltier element 2.

The measuring manifold for the determination of the temperature corresponding to a dew-point of a humid gas sample consists of pressure lines with an inlet I and an outlet O. The humid gas sample, the humidity of which is to be determined by measuring the temperature of its dew-point, enters the measuring manifold at I. From the inlet I, via the gas circuit 22 and 22', the humid gas sample streams to and from the dew-point mirror 3, respectively.

In a by-pass 23, also consisting of pressure lines, which optionally connects the gas outlet line 22' with its inlet line 22, are arranged in series a gas valve 24, an injection pump 25 and the humidification unit 26. The gas valve 24 comprises a commercially available needle valve (Swagelock, trademark of Crowford Fitting Company, Ont. Canada) to control the flowrate through the bypass and a non-return valve to prevent backflow through the bypass, also commercially available. The injector pump 25 may be a positive displacement piston pump, such as a suction-pressure pump of series G-07 of Helmut Brey GmbH & Co. KG, D8940 Memmingen (Leaflet BO9/85-2). For use with high pressures, a high-pressure pump is used (MBW ELEKTRONIK AG, CH-5430 Wettingen, Leaflet February 1985). With this high-pressure pump, maximum pressure of the sample gas can be as high as 200 bar.

Figure 3:
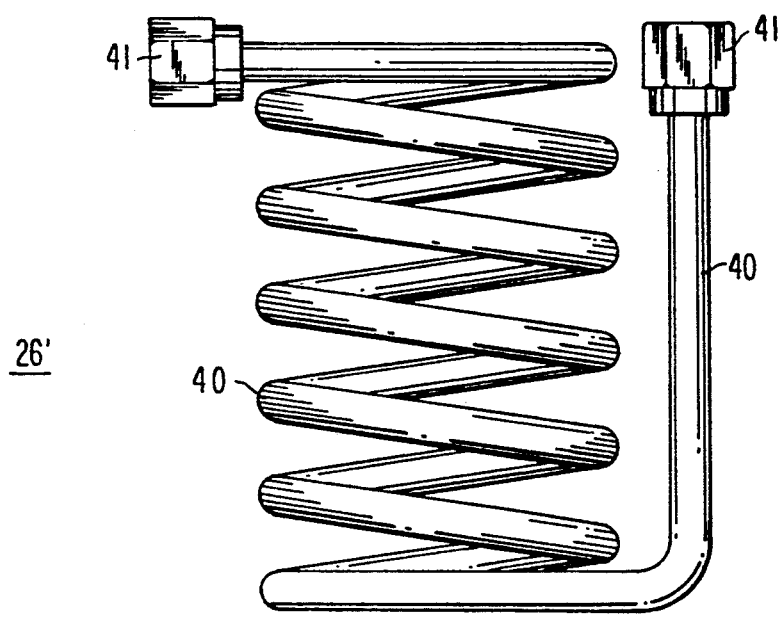
FIG. 3 shows a helical tube for humidification without external accessories.

The humidification unit 26' (FIG. 3) may be a helically wound tubular duct 40 made of a hygroscopic polyamide. Ambient humidity diffuses through the walls of the tubular duct 40 and admixes with the gas flowing through it. To increase the duct surface which increases the humidity to be added to the gas through diffusion through the duct surface, the duct may be helically wound. The gas flowing through this duct is sufficiently humidified.

Favorable experience was had with a duct 40 made of Ertalon (Trademark for a polyamide made by Erta, Tielt, Belgium), having a total length of 1200 mm, an internal diameter of 4 mm and an external diameter of 6 mm. The ends are provided with commercially available threaded tube fittings, including gripper rings (not shown). The helical shape is easily produced by winding onto an aluminum body and subsequent heating to 120° C. for two hours.

The injector pump 25 is controlled by the automatic dew-point mirror control unit 17. As soon as a preselected temperature is attained the injector pump is activated. Then, via the gas valve 24, a volume of about 0.5 $cm^3$ of gas from the humidification unit is injected into the inlet line 22 to combine with the normal flow and contact the dew-point mirror.

The preselected temperature at which the above injection takes place should lie at least 10° below the temperature corresponding to the expected dew-point of the gas under measurement, with injection preferably performed at a preselected temperature of 10° C. to 20° C. below the expected dew-point temperature. However, if a very low dew-point temperature is foreseen, injection can be carried out at the lowest mirror temperature attainable, i.e. at 178K (corresponds to −95° C). It is also possible to inject at a temperature above the expected dew-point. As the humidity of the humid gas sample is raised upon injection from the humidification unit, its dew point is also raised, which will cause a dew layer to form on the mirror at a higher temperature. The formation of the dew layer, however, may be at a somewhat slower rate than at a lower temperature.

The gas injected out of the humidification unit is a portion of the humid gas sample under measurement which previously passed the dew-point mirror 3 and streamed through the line 22' into the by-pass 23 to enter the humidification unit 26, where it is enriched in humidity, i.e. the water molecules from ambient atmosphere diffuse through the walls of the tubular duct and admix with the gas, thus adding excess moisture to it.

When this gas, enriched in humidity and blended with the humid gas sample entering the manifold through input I, passes the dew-point mirror which is at its preselected, preferably low temperature, a detectable dew or hoar layer immediately forms on the mirror surface. After completing the injection, the valve 24 closes, which disconnects the by-pass 23 from the inlet line 22. Again, only the humid gas sample whose dew-point is to be determined passes across the dew-point mirror.

This humid gas sample under measurement typically has a humidity content ranging between 0.04 ppm to about 38 ppm; the dew-point temperatures for these concentrations of humidity normally lie between 178K and 223K. The humid gas sample streams through the manifold and across the dew-point mirror at a rate of 20 to 40 liter/hour at normal pressure.

When the bypass 23 is disconnected from the inlet line 22 and the humid gas sample alone again streams across the dew-point mirror, now covered with a coat of dew, the humid gas sample absorbs the deposited dew from the surface of the mirror, due to the prerequisite equilibrium in the system, and carries the absorbed dew away in its stream. As a result, the surface of the mirror no longer has a layer of dew which is detectable by the light beam—only a very thin layer of water molecules adhering to the surface of the mirror is left. These molecules, when the real dew-point temperature which corresponds to the humidity of the humid gas sample under measurement is reached, serve as initiators or crystallizing centers for the condensed water vapors to form a new detectable dew coat on the surface of the mirror, thus allowing a detectable dew layer to adhere to the mirror in a relatively short period of time when the dew point is reached.

Following the above described process, or running concurrently with it, the temperature of the dew-point mirror is slowly raised by the Peltier element 2 if the temperature of the mirror was below the expected dew-point. The reflection of the light beam is followed for a change in its angle, which indicates the formation of a stable dew layer on the dew-point mirror 3. Since the system may be regarded as a closed system at equilibrium reigning between the gas phase and the surface of the dew-point mirror, it may be possible to reach the temperature of dew-point either from above, by lowering the temperature of streaming gas, or from below, by heating the surface of the dew-point mirror.

The attainment of the dew-point is indicated by a constant, stable temperature. It is to be kept in mind, that as described previously, the heating or respective cooling of the Peltier element is controlled by the automatic mirror control unit 17 in a per se known manner. Hence a constant temperature indicates a steady, unchanging layer of dew.

Figure 2A:
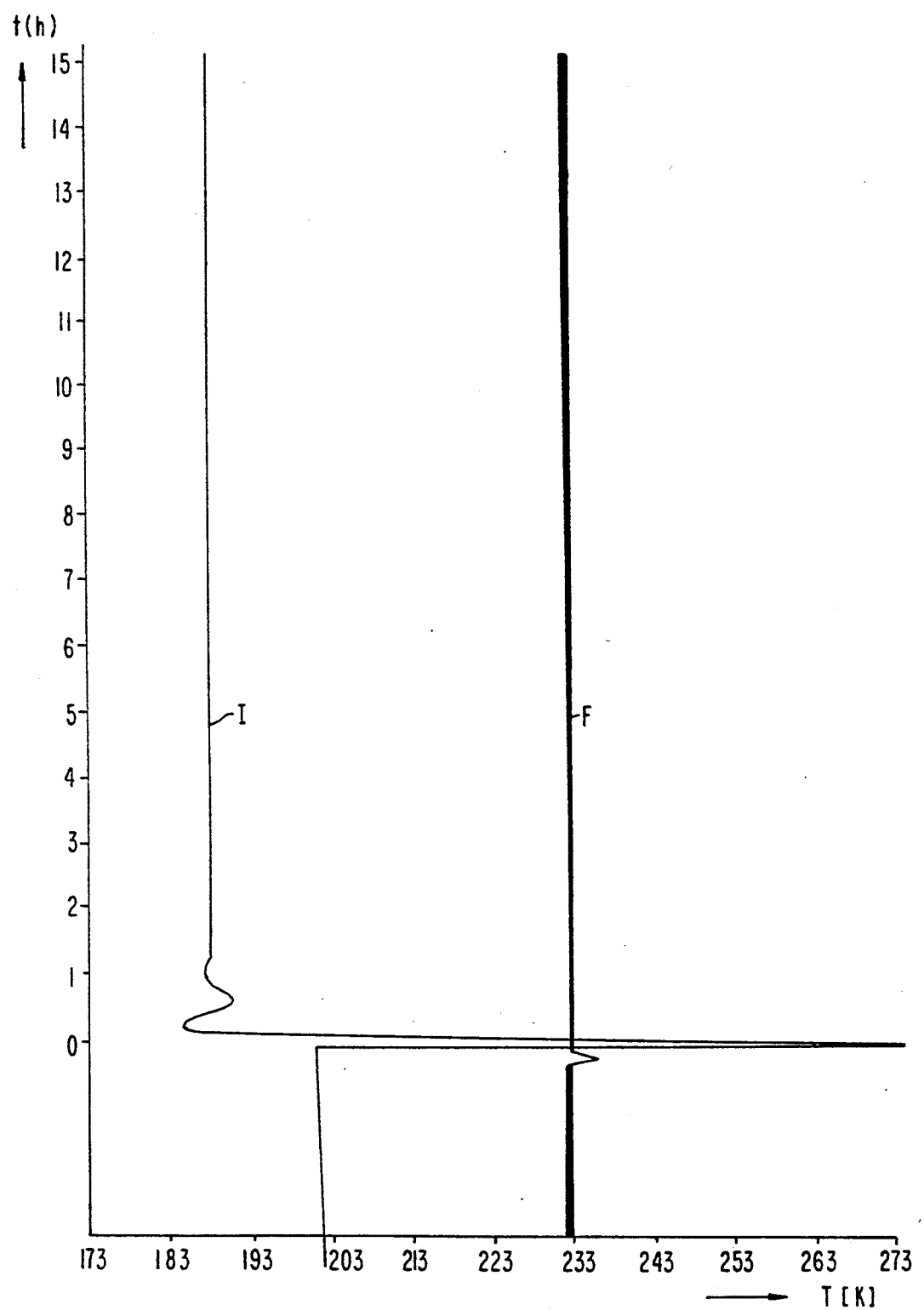
FIG. 2a is a graphic recording of measured temperature vs. time during dew-point determination of a gas excess moisture added to the gas according to the present invention.

FIG. 2a is a recording of measured temperature T in K on the abscissa as function of time in hours (h) on the ordinate needed for the measurement of dew-point. The heavier line F, at 233K, is the recorded temperature course of a Freon precooler which is here used instead of the water cooler 7 as assisted by the fan 8. This precooler shows a high temperature stability and results in a very accurate measurement.

Curve I in FIG. 2a shows the recorded temperature as a function of time during the dew-point determination with an injection of access humidity during the measurement, according to the invention.

Figure 2B:
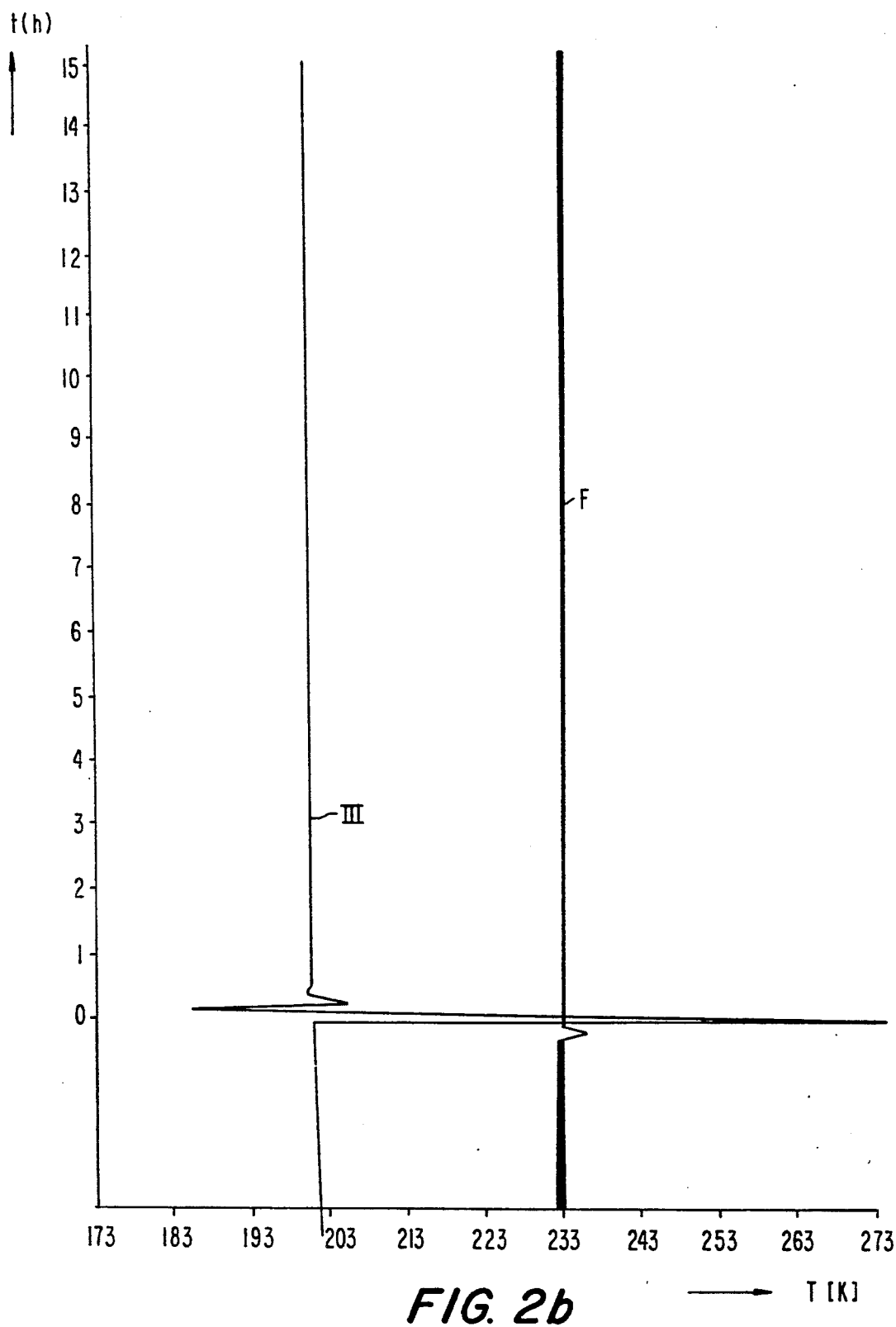
FIG. 2b represent measurements corresponding to those of FIG. 2a, but with a second gas.

Curve III in FIG. 2b shows the recorded temperature as a function of time during the dew-point determination of a second gas, with an injection of access humidity during the measurement, according to the invention.

It is clearly evident, that applying the method of measurement described by the invention, in the first example of FIG. 2a, a reduced time of measurement to 1.5 hours was obtained. In the second example of FIG. 2b a reduction to 45 minutes was achieved by applying the method of invention.

The transients in the course of recorded temperatures seen in the diagrams are the results of the per se known automatic dew-point mirror cleaning.

The invention has proved to be most advantageous for the continuous measurement of dew-point temperatures such as needed for supervision.

While presently preferred embodiments of the present invention have been shown and described, it is apparent that various changes and modifications may be made therein without departing from the invention. Therefore, it is intended in the appended claims to cover all such changes and modifications as fall within the true spirit and scope of the claims.

I claim:

1. A method for determination of the dew point of a humid gas sample with a dew point less than 273K. by means of the sensing of a light beam reflected by a dew point mirror comprising the steps of:

passing a gas having a humidity level above that of the humid gas sample across said mirror to form a detectable dew layer upon said mirror;

removing said detectable dew layer from said mirror to leave a non-detectable layer of water molecules thereon to serve as an initiator for the formation of a subsequent detectable dew layer; and passing said humid gas sample across said mirror while adjusting the temperature of said mirror to the point at which a detectable dew layer reappears on said mirror, whereby the dew point of said humid gas sample is determined.

2. The method of claim 1 further including the step of forming said gas having a humidity level above that of said humid gas sample by injecting additional moisture into a portion of said humid gas sample.

3. The method of claim 2, wherein said forming step comprises the steps of conducting said humid gas sample to and from said mirror and injecting said additional moisture into a portion of said humid gas sample obtained from the humid gas sample being conducted from said mirror.

4. The method of claim 1, wherein said step of passing said increased humidity gas across said mirror is performed at a mirror temperature below the expected dewpoint of said humid gas sample.

5. The method of claim 4, wherein said step of removing said sensed dew layer comprises raising the temperature of said mirror to a point above the expected dew-point of said humid gas sample.

6. The method of claim 1, wherein said step of passing said increased humidity gas across said mirror is performed at a mirror temperature above the expected dewpoint of said humid gas sample.

7. The method of claim 5 or claim 6, wherein said step of removing said sensed dew layer comprises the passing of said humid gas sample across said mirror.

8. A device for the determination of the dew point of a humid gas sample with a dew point less than 273K. by means of the sensing of a light beam reflected from a dew point mirror, the temperature of which is variable, comprising means for passing a humidity-enriched gas over said mirror to form a detectable dew layer thereon; means for removing said detectable dew layer therefrom while keeping a non-detectable layer of water molecules thereon to serve as an initiator for the reformation of dew thereon, means for passing a humid gas sample across said mirror, and means for adjusting the temperature of said mirror while said humid gas is passed thereacross, whereby the dew point of said humid gas sample may be determined by the re-establishment of a detectable dew layer on said mirror.

9. The apparatus of claim 8, wherein said means for passing said humid gas sample across said mirror comprises a supply line to said mirror and a removal line from said mirror.

10. The apparatus of claim 9, wherein said means for passing an increased humidity gas sample across said mirror comprises a humid gas sample humidification unit having an input coupled to said removal line and an output coupled to said supply line.

11. The apparatus of claim 10, wherein said humidification unit comprises a hygroscopic tubular duct.

12. The apparatus of claim 11, wherein said humidification unit further comprises an injector pump and valve means.

13. The apparatus of claim 11, wherein said tubular duct is formed of a polyamide.

* * * * *